United States Patent [19] [11] 3,963,701
Grisar et al. [45] June 15, 1976

[54] SUBSTITUTED BENZHYDRYL
LACTAMIMIDE DERIVATIVES

[75] Inventors: Johann Martin Grisar; Norbert Leonard Wiech, both of Cincinnati, Ohio

[73] Assignee: Richardson-Merrell Inc., Wilton, Conn.

[22] Filed: Aug. 27, 1973

[21] Appl. No.: 391,573

Related U.S. Application Data

[63] Continuation-in-part of Ser. No. 244,873, April 17, 1972, abandoned.

[52] U.S. Cl. .................. 260/239 B; 260/239 BE; 260/293.73; 260/293.78; 260/294.8 G; 260/296 R; 260/326.55; 260/326.5 L; 260/326.8; 260/326.85; 260/326.9; 424/244; 424/263; 424/267; 424/274
[51] Int. Cl.² ............ C07D 207/22; C07D 211/72; C07D 223/12
[58] Field of Search ..... 260/239 B, 239 BE, 293.73, 260/293.78, 326.85, 294.8 G, 296 R, 296 AE, 326.5 L, 326.5 S, 326.82, 326.85, 326.9

[56] References Cited
UNITED STATES PATENTS
3,725,435 4/1973 Poos ........................... 260/326.85

FOREIGN PATENTS OR APPLICATIONS
1,210,848 11/1970 United Kingdom ............ 260/239 B

*Primary Examiner*—Alton D. Rollins
*Attorney, Agent, or Firm*—L. Ruth Hattan; Eugene O. Retter; George W. Rauchfuss, Jr.

[57] ABSTRACT
Novel compounds useful as diuretic agents and anticoagulants are represented by the following formula

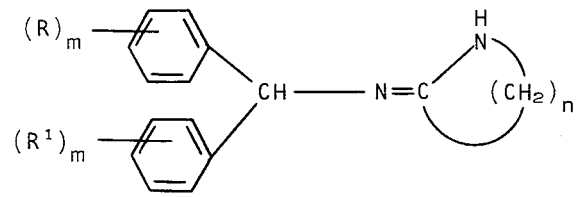

wherein $m$ is a positive whole integer of from 1 to 3; $n$ is a positive whole integer of from 3 to 7; R and $R^1$ may be the same or different and represent hydrogen, a straight or branched lower alkyl chain of from 1 to 4 carbon atoms, halogen, trifluorometyl, trifluoromethylthio, trifluoromethoxy, phenyl, phenoxy, or lower alkoxy of from 1 to 4 carbon atoms, with the proviso that both R and R' are not hydrogen, and with the proviso that when $m$ is equal to 1, and one of R or $R^1$ is hydrogen the other of R or $R^1$ is not lower alkoxy of from 1 to 4 carbon atoms; and pharmaceutically acceptable acid addition salts and individual optical isomers where applicable.

9 Claims, No Drawings

SUBSTITUTED BENZHYDRYL LACTAMIMIDE DERIVATIVES

This application is a continuation in part of copending application Ser. No. 244,873 filed, Apr. 17, 1972, now abandoned.

FIELD OF INVENTION

This invention relates to novel substituted benzhydryl lactamimides useful as diuretic agents and anticoagulants and to methods of using these compounds.

SUMMARY OF INVENTION

The novel compounds of this invention are represented by the following Formula I:

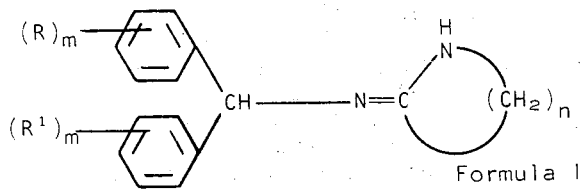

Formula I wherein $m$ is a positive whole integer of from 1 to 3; $n$ is a positive whole integer of from 3 to 7; R and $R^1$ may be the same or different and represent hydrogen, a straight or branched lower alkyl chain of from 1 to 4 carbon atoms, halogen, trifluoromethyl, trifluoromethylthio, trifluoromethoxy, phenyl, phenoxy, or lower alkoxy of from 1 to 4 carbon atoms, with the proviso that both R and $R^1$ are not hydrogen, and with the proviso that when $m$ is 1 and one of R or $R^1$ is hydrogen, the other of R or $R^1$ is not lower alkoxy of from 1 to 4 carbon atoms. The substituent groups as represented by R and $R^1$ may be attached to the ortho, meta, or para positions of the phenyl rings. This invention also includes pharmaceutically acceptable acid addition salts and individual optical isomers where applicable.

DETAILED DESCRIPTION OF INVENTION

For convenience and uniformity all the compounds of this invention are named and represented as 2-iminoperhydroazacarbocyclics, as represented by Formula I. However, it is known that compounds of this type may also be represented by the tautomeric form illustrated by the following Formula II:

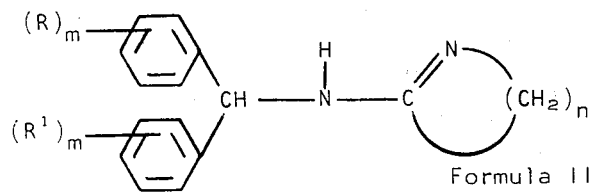

Formula II

This tautomerism has been discussed by R. Kwok and P. Pranc, J. Org. Chem. 32, 740 (1967). Compounds of Formula II may be named differently. In solution under the conditions of therapeutic utility, the proportion of each tautomeric form, or the delocalization of the charge between the two nitrogens, will be dependent upon numerous factors including the nature of the substituents, the pH of the medium, and the like. This equilibrium state is conveniently depicted by the following Formula III:

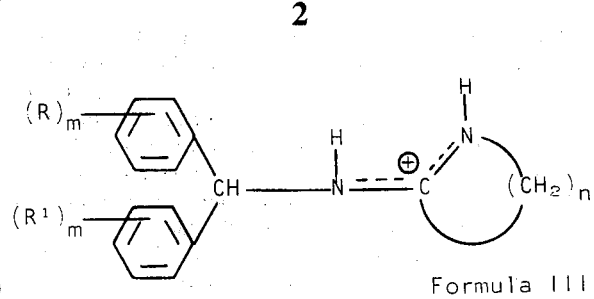

Formula III

This invention relates to compounds represented or named in either tautomeric form.

Preferred compounds of this invention are those of general Formulas I to III wherein R and $R^1$ represent hydrogen, a straight or branched lower alkyl chain of from 1 to 4 carbon atoms, halogen, or trifluoromethyl with the proviso that both R and $R^1$ are not hydrogen.

In each of the general formulas I to III, $n$ represents an integer of from 3 to 7, $m$ represents an integer of from 1 to 3, and R and $R^1$ represent hydrogen, a straight or branched lower alkyl chain of from 1 to 4 carbon atoms such as, for example, methyl, ethyl, propyl, isopropyl, butyl, tertiary butyl and the like, halogen, that is, bromine, chlorine, fluorine, or iodine, trifluoromethyl, trifluoromethylthio, trifluoromethoxy, phenyl, phenoxy, a lower alkoxy group of from 1 to 4 carbon atoms, such as, for example, methoxy, ethoxy, propoxy, and the like. In general Formulas I to III both R and $R^1$ cannot be hydrogen, and the substituent groups as represented by R and $R^1$ may be attached at the ortho, meta or para positions of the phenyl rings. Also in Formulas I to III when $m$ is equal to 1 and one of R or $R_1$ is hydrogen, the other of R or $R_1$ cannot be lower alkoxy of from 1 to 4 carbon atoms.

As examples of compounds of this invention there may be mentioned.

2-[(bis{p-ethylphenyl}methyl)imino]octahydroazocine,

2-[(p-chloro-α-phenylbenzyl)imino]hexahydroazepine, hexahydro-2-[(α-{m-methylphenyl}-m-isopropylbenzyl)imino]-octahydroazonine, 2-[(bis{p-trifluoromethylthiophenyl}methyl)imino]-piperidine, hexahydro-2-[(m-{trifluoromethyl}-α-phenylbenzyl)imino]-azepine, 2-[(p-chloro-α-{p-chlorophenyl}benzyl)imino]hexahydroazepine, 2-[(α-{p-chlorophenyl}-m-trifluoromethylbenzyl)imino]-hexahydroazepine, 2-[(p-tert-butyl-α-{p-chlorophenyl}benzyl)imino]-pyrrolidine, hexahydro-2-[(α-phenyl-p-trifluoromethoxybenzyl)imino]-azepine, 2-[(p-bromo-α-phenylbenzyl)imino]hexahydroazepine, hexahydro-2-[(p-phenoxy-α-phenylbenzyl)imino]azepine, hexahydro-2-[(3,4,5-trimethoxy-α-phenylbenzyl)imino]-azepine, hexahydro-2-[(3,4,-dipropoxy)α-phenylbenzyl)imino]azepine, and the like.

Pharmaceutically acceptable acid addition salts of the base compounds of this invention are those of any suitable inorganic or organic acid. Suitable inorganic acids are, for example, hydrochloric, hydrobromic, sulfuric, or phosphoric acids and the like. Suitable organic acids are, for example, carboxylic acids such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicylic, 2-phenoxybenzoic and the like, or sulfonic acids such as methane sulfonic, 2-hydroxyethane sulfonic acid and the like.

The compounds of this invention including acid addition salts and individual optical isomers where applicable are useful as diuretic agents and anticoagulants. The compounds of this invention can be administered to animals, particularly warm blooded animals, mammals, and humans, either alone or in the form of pharmaceutical preparations which contain the novel compounds suitable for oral or parenteral administration. Pharmaceutical preparations containing novel compounds of this invention and conventional pharmaceutical carriers can be employed in unit dosage forms such as solids, for example, tablets and capsules, or liquid solutions, suspensions or elixirs for oral administration, or liquid solutions, suspensions, emulsions, and the like for parenteral use. The quantity of compound administered can vary over a wide range to provide from about 0.1 mg/kg (milligram per kilogram) to about 50 mg/kg of body weight of the patient per day to achieve the desired effect. Unit doses of these compounds can contain from about 5 to 250 mg of the compound and may be administered, for example, from 1 to 4 times daily.

Summarized in Table I are diuretic data for compounds of this invention which were obtained by orally administering the indicated compounds to rats and measuring in milliliters at 5 hours the per cent increase in urine excretion over that of control rats. The Example numbers in Table I correspond to the Example numbers of the specific examples used to illustrate the invention.

Table 1

| Example No. | Dose mg/kg | % Urine Increase |
|---|---|---|
| 1 | 25 | 273 |
|  | 10 | 242 |
| 2 | 25 | 796 |
|  | 10 | 414 |
| 3 | 25 | 705 |
|  | 10 | 195 |
| 4 | 25 | 732 |
| 5 | 25 | 303 |
| 11 | 25 | 264 |
| 14 | 25 | 242 |

To illustrate the anticoagulant activity of the compounds of this invention the compound of Example 18 demonstrated in vitro a 95% inhibition of adenosine diphosphate induced platelet aggregation in human platelet rich plasma when 100 μg of compound was added to each milliliter of plasma.

The compounds of Formula I may be prepared by reacting an excess of a lactim ether of the general formula

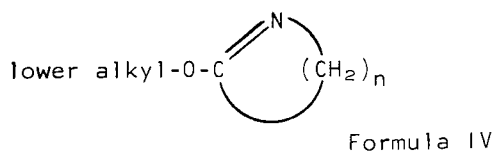

Formula IV with a primary amine of the following general formula

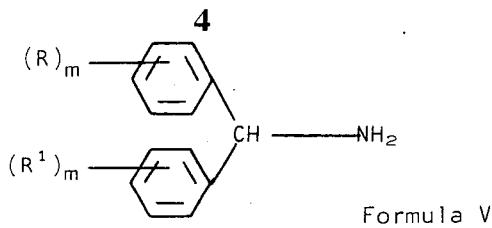

Formula V in a manner similar to that reported by R. E. Benson and T. L. Cairns in J. Am. Chem. Soc. 70, 2115–8 (1948). The symbols R, R¹, n and m have the meanings defined hereinbefore and lower alkyl may be methyl, ethyl or the like. This reaction may be carried out with or without a solvent. When a solvent is used that preferred is a lower alcohol; however, other solvents such as benzene, toluene and the like may be used. A basic or an acidic catalyst such as a tertiary amine or hydrogen chloride may be added to the reaction mixture. In general it is preferred that the hydrochloride salt of the amine be used in the reaction. The temperature of the reaction varies from −40°C to 180°C, and the preferred temperature is about 15°–25°C. The reaction time varies from 1 hour to about 60 days being dependent upon the temperature of the reaction, the reactant primary amine, and more particularly on the degree of steric hindrance of the amine since highly sterically hindered amines react very slowly.

The lactim ethers which find use in this reaction may be prepared from commercially available corresponding lactams by methods known in the art. For example, by reaction of an appropriate lactam with dimethyl sulfate in a solvent such as benzene, toluene, xylene or the like at the reflux temperature of the solvent for 2–24 hours the corresponding O-methyl lactim ether is obtained.

The primary amines which find use in this invention are benzhydrylamines of the following structure:

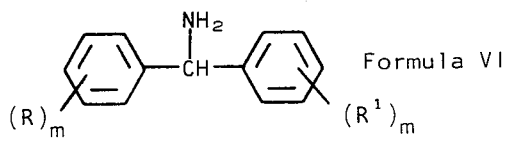

Formula VI

Several methods of preparing benzhydrylamines are known to the art. An excellent method, particularly suited to prepare unsymmetrically substituted benzhydrylamines consists of reacting phenyl or a (substituted)-phenyl magnesium halide with benzonitrile or a (substituted)-benzonitrile and to reduce the resulting ketimine complex in situ with lithium aluminum hydride. A number of methods are available to convert benzophenones (VII)

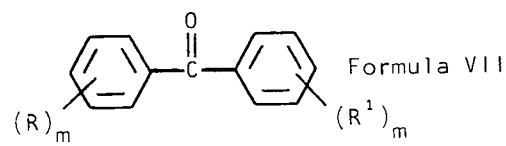

Formula VII to benzhydrylamines either directly, for instance by the Leuckart reaction or a variation thereof, or indirectly by way of the oximes (VIII)

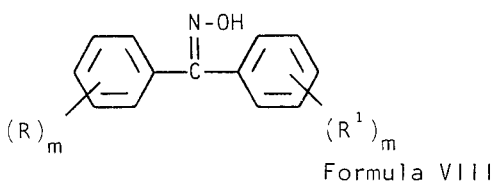

Formula VIII formed from benzophenones and hydroxylamine, using a reducing agent such as lithium aluminum hydride, sodium in alcohol or molecular hydrogen in the presence of a noble metal catalyst, preferably rhodium-on-charcoal.

In the above formulas VI, VII, and VIII, R, R¹ and $m$ having the meanings defined hereinbefore.

The compounds of this invention may also be prepared using a complex of an appropriate lactam of the formula Formula IX wherein $n$ has the meaning defined hereinbefore, with phosphorus oxychloride, phosgene, borontrifluoride etherate, dimethyl sulfate, hydrogen halide or a combination of two or more such reagents. Several attempts have been made to formulate the structure of these complexes, and one formulation includes the vinyl halide, that is, 2-chloro-4,5,6,7-tetrahydro-3H-azepine. However, none of the formulations have been unambiguously established. This reaction has been studied by H. Bredereck in a series of articles in Chem. Ber., 1953–1968, particularly in vol. 94, 2278 (1961) and vol. 97, 1403 (1964). The complex formed is reacted with an appropriate primary amine described hereinabove in an aromatic hydrocarbon solvent such as benzene, toluene or xylene or an alkyl polyhalide solvent such as carbon tetrachloride, chloroform, methylene chloride, dichloroethane, tetrachloroethylene or the like. The reaction temperature is limited by the boiling point of the solvent, however, in some cases it is advantageous to carry out the reaction at room temperature or with cooling at 0° to −40°C depending on the reactants.

Similarly the above reaction may be carried out by using known thiolactim ethers such as S-methylthiocaprolactim [H. Behringer and H. Meier. Ann. 607, 73-91 (1957)], or by using thiolactams wherein the latter case it may be advantageous to employ a catalyst such as mercury or silver oxide or cyanide [J. Gauthier and J. Renault, C.R. Acad. Sci. 234, (1952)].

Also by catalytic hydrogenation of an appropriate amino-pyridine derivative as described by T. Grave, J. Am. Chem. Soc. 46, 1460 (1924), M. Friefelder et al., J. Org. Chem. 29, 3730 (1964) and L. Birkhofer, Ber. 75, 429 (1942), compounds of this invention containing a pentamethylenimine moiety may be obtained.

The following specific examples are illustrative of the invention.

EXAMPLE 1

2-[(p-Chloro-α-phenylbenzyl)imino]hexahydroazepine hydrochloride

A slurry of 12.0 g of 4-chlorobenzhydrylamine hydrochloride in 23 ml of O-methylcaprolactim was allowed to stand at room temperature for 3 days and was stirred occasionally with a glass rod. At first, the mixture became nearly homogeneous and then it began to solidify. Small amounts of anhydrous ethanol were added to keep the mixture in a stirrable slurry. The mixture was then cooled, the solid was collected and washed with ether and was recrystallyzed twice from methanol-acetone to give 11.7 g of the title compound, m.p. 238°–240°C. The identity of the compound was confirmed by micro-analysis, infrared and ultraviolet spectra.

EXAMPLE 2

Hexahydro-2-[(m-{trifluoromethyl}-α-phenylbenzyl)imino]-azepine Hydrochloride

A. To m-trifluoromethylphenylmagnesium bromide, prepared from 4.66 g of magnesium turnings and 40.7 g of m-bromo-benzotrifluoride in approximately 200 ml of anhydrous ether, was added dropwise a solution of 16.5 g of benzonitrile in 30 ml of anhydrous ether. The mixture was refluxed for 2 hours and was allowed to stand overnight. The resulting partly heterogeneous mixture of ketimine salt was added in portions over ½ hour to a slurry of 7.25 g of lithium aluminum hydride under 800 ml of anhydrous ether and the mixture was stirred and refluxed overnight. It was decomposed by carefully adding, over a period of 4 hours, 7.25 ml of water, followed by 7.25 ml of 15% sodium hydroxide solution, followed by 22 ml of water. The resulting precipitate of inorganic material was filtered off and washed with ether and to the filtrate was added 350 ml of 10% hydrochloric acid and 200 ml of water. A heavy precipitate formed that was collected and washed with ether, 38.3 g (83% yield), m.p. 267°–270°C (dec.). A small sample was recrystallized twice from isopropanol, m.p. 278°–279°C. Microanalysis and infrared spectrum were consistent with the structure of α-phenyl-m-(trifluoromethyl)benzylamine hydrochloride. B. By the procedure of Example 1, only substituting for 4-chlorobenzhydrylamine hydrochloride, an appropriate amount of the above amine hydrochloride, the desired product was obtained, m.p. 237°–238°C. Its structure was confirmed by microanalysis and spectra.

By the procedure described in Example 2 (A) the following benzhydrylamines were prepared:

2-methylbenzhydrylamine hydrochloride, m.p. 309.5°–311.5°C, 4,4'-dichlorobenzhydrylamine hydrochloride, m.p. 293.5°–297°C, α-(p-chlorophenyl)-3-trifluoromethylbenzylamine hydrochloride, m.p. 279°–282°C, 3,3'-trifluoromethylbenzhydrylamine hydrochloride, m.p. 293°–294°C.

2-chlorobenzhydrylamine hydrochloride, m.p. 276.5°–277.5°C, 3-chlorobenzhydrylamine hydrochloride, m.p. 292°–293°C, 4-fluorobenzhydrylamine hydrochloride, m.p. 306°–307°C, 4-trifluoromethylthiobenzhydrylamine hydrochloride, m.p. 248°–254°C, 4-trifluoromethoxybenzhydrylamine hydrochloride, m.p. 269°–270°C, 4-trifluoromethylbenzhydrylamine hydrochloride, m.p. >305°C, 4-bromobenzhydrylamine hydrochloride, m.p. 292°–294°C, 3,4-dimethoxybenzhydrylamine hydrochloride, m.p. 246°–248°C, 3,4,5-trimethoxybenzhydrylamine hydrochloride, m.p. 227°–229°C, 4-isopropylbenzhydrylamine hydrochloride, m.p. 240°–243°C, α-(biphenylyl)benzylamine hydrochloride, m.p. 273.5°–275.5°C, 4-phenoxybenzhydrylamine hydrochloride, m.p. 222°–223°C, 2-trifluoromethylbenzhydrylamine hydrochloride, m.p. 191°–196°C, By the general procedure of Example 1, only substituting for 4-chlorobenzhydrylamine hydrochloride respectively an appropriate amount of each of the above benzhydrylamine hydrochlorides the compounds in the following Table II are obtained.

Table 11

| Example No. | Compound Name, m.p. |
|---|---|
| 3 | Hexahydro-2-[(o-methyl-α-phenylbenzyl)imino]-azepine hydrochloride, m.p. 274.5–276°C. |
| 4 | 2-[(p-Chloro-α-{p-chlorophenyl}benzyl)imino]-hexahydroazepine hydrochloride, m.p. 254.5–256.5°C. |
| 5 | 2-[(α-{p-Chlorophenyl}-m-trifluoromethylbenzyl)imino]hexahydroazepine hydrochloride, m.p. 248.5–250.5°C. |
| 6 | Hexahydro-2-[(bis{m-triflouromethylphenyl}-methyl)imino]azepine hydrochloride, m.p. 260–261.5°C. |
| 7 | 2-[(o-Chloro-α-phenylbenzyl)imino]hexahydro-azepine hydrochloride, m.p. 269–270°C. |
| 8 | 2-[(m-Chloro-α-phenylbenzyl)imino]hexahydro-azepine hydrochloride, m.p. 278–279°C. |
| 9 | 2-[(p-Fluoro-α-phenylbenzyl)imino]hexahydro-azepine hydrochloride, m.p. 237.5–238°C. |
| 10 | Hexahydro-2-[(α-phenyl-p-{trifluoromethylthio}benzyl)imino]azepine hydrochloride m.p. 206–209°C. |
| 11 | Hexahydro-2-[(α-phenyl-p-{trifluoromethoxy}-benzyl)imino]azepine hydrochloride, m.p. 190–193°C. |
| 12 | Hexahydro-2-[(α-phenyl-p-{trifluoromethyl}-benzyl)imino[azepine hydrochloride, m.p. 208–209°C. |
| 13 | 2-[(p-Bromo-α-phenylbenzyl)imino]hexahydro-azepine hydrochloride, m.p. 233–234°C. |
| 14 | Hexahydro-2-[(3,4-dimethoxy-α-phenylbenzyl)-imino)azepine hydrochloride, m.p. 236–238°C. |
| 15 | Hexahydro-2-[(3,4,5-trimethoxy-α-phenylbenzyl)imino]azepine hydrochloride, m.p. 239–241°C. |
| 16 | Hexahydro-2-[(p-isopropyl-α-phenylbenzyl)-imino]azepine hydrochloride, m.p. 203–206°C. |
| 17 | 2-[α-(p-biphenylyl)benzylimino]hexahydro-azepine hydrochloride, m.p. 264.5–266°C. |
| 18 | Hexahydro-2-[(p-phenoxy-α-phenylbenzyl)imino]-azepine hydrochloride, m.p. 200.5–202.5°C. |
| 19 | Hexahydro-2-[(α-phenyl-2-trifluoromethylbenzyl)imino]azepine hydrochloride, m.p. 227–229°C. |

EXAMPLE 20

2-[(p-Fluoro-α-phenylbenzyl)imino]piperidine hydrochloride

By the procedure of Example 1, only substituting respectively for 4-chlorobenzhydrylamine and O-methylcaprolactim, appropriate amounts of 4-fluorobenzhydrylamine and O-methylvalerolactim the title compound was obtained, m.p. 211°–213°C.

EXAMPLE 21

An illustrative composition for tablets is as follows:

|     |                                                                  | Per Tablet |
|-----|------------------------------------------------------------------|------------|
| (a) | 2-[(p-chloro-α-phenylbenzyl)imino]-hexahydroazepine hydrochloride | 100.0 mg   |
| (b) | wheat starch                                                     | 15.0 mg    |
| (c) | lactose                                                          | 33.5 mg    |
| (d) | magnesium stearate                                               | 1.5 mg     |

A portion of the wheat starch is used to make a granulated starch paste which together with the remainder of the wheat starch and the lactose is granulated, screened and mixed with the active ingredient, that is, (a), and the magnesium stearate. The mixture is compressed into tablets weighing 150 mg each.

EXAMPLE 22

An illustrative composition for a parenteral injection is the following wherein the quantities are on a weight to volume bases.

|     |                                                                  | amount   |
|-----|------------------------------------------------------------------|----------|
| (a) | hexahydro-2-[(o-methyl-α-phenylbenzyl)imino]azepine hydrochloride | 100.0 mg |
| (b) | sodium chloride                                                  | q.s.     |
| (c) | water for injection to make                                      | 10.0 ml  |

The composition is prepared by dissolving the active ingredient, that is (a), and sufficient sodium chloride in water for injection to render the solution isotonic. The composition may be dispensed in a single ampule containing 100 mg of the active ingredient for multiple dosage or in 10 ampules for single dosage.

EXAMPLE 23

An illustrative composition for hard gelatin capsules is as follows:

|     |                                                                                       | Per Capsule |
|-----|---------------------------------------------------------------------------------------|-------------|
| (a) | hexahydro-2-[(m-{trifluoromethyl}-α-phenylbenzyl)imino]azepine hydrochloride           | 200.0 mg    |
| (b) | talc                                                                                  | 35.0 mg     |

The composition is prepared by passing the dry powders of (a) and (b) through a fine mesh screen and mixing them well. The powder is then filled into No. 0 hard gelatin capsules at a net fill of 235 mg per capsule.

We claim:

1. A compound selected from a base of the formula

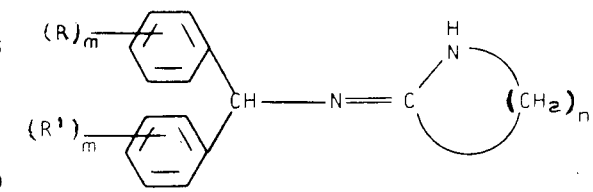

wherein m is a positive whole integer of from 1 to 3; n is a positive whole integer of from 3 to 7; each of R and R¹ is selected from the group consisting of hydrogen, a straight or branched lower alkyl chain of from 1 to 4 carbon atoms, a halogen atom, trifluoromethyl, trifluoromethylthio, trifluoromethoxy, phenyl, phenoxy, a lower alkoxy group of from 1 to 4 carbon atoms, with the proviso that both R and R¹ are not hydrogen and with the proviso that when m is equal to 1 and one of R and R¹ is hydrogen, the other of R or R¹ is not lower alkoxy of from 1 to 4 carbon atoms; and pharmaceutically acceptable acid addition salts thereof.

2. A compound of claim 1 wherein each of R and R¹ is selected from the group consisting of a straight or branched lower alkyl chain of from 1 to 4 carbon atoms, a halogen atom, trifluoromethyl, trifluoromethylthio trifluoromethoxy, phenyl, phenoxy and a lower alkoxy group of from 1 to 4 carbon atoms.

3. A compound of claim 2 wherein n is the integer 4 or 5.

4. A compound of claim 3 which is 2-[(α-{p-chlorophenyl}-m-trifluoromethylbenzyl)imino]hexahydroazepine and pharmaceutically acceptable acid addition salts thereof.

5. A compound of claim 1 wherein R is hydrogen and R¹ is selected from the group consisting of a straight or branched lower alkyl chain of from 1 to 4 carbon atoms, a halogen atom, trifluoromethyl, trifluoromethylthio, trifluoromethoxy, phenyl, phenoxy, and a lower alkoxy group of from 1 to 4 carbon atoms with the proviso that when m is equal to 1, R¹ is not a lower alkoxy group of from 1 to 4 carbon atoms.

6. A compound of claim 5 wherein $n$ is the integer 4 or 5.

7. A compound of claim 6 which is 2-[(p-chloro-α-phenylbenzyl)imino]hexahydroazepine and pharmaceutically acceptable acid addition salts thereof.

8. A compound of claim 6 which is hexahydro-2-[(m-{trifluorometyl}-α-phenylbenzyl)imino]azepine and pharmaceutically acceptable acid addition salts thereof.

9. A compound of claim 6 which is hexahydro-2-[(o-methyl-α-phenylbenzyl)imino]azepine and pharmaceutically acceptable acid addition salts thereof.

* * * * *